US006360608B1

(12) United States Patent
Dunegan

(10) Patent No.: US 6,360,608 B1
(45) Date of Patent: *Mar. 26, 2002

(54) TRANSDUCER FOR MEASURING ACOUSTIC EMISSION EVENTS

(75) Inventor: Harold L. Dunegan, Laguna Niguel, CA (US)

(73) Assignee: Dunegan Engineering Consultants, Inc., San Juan Capistrano, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/519,497

(22) Filed: Mar. 6, 2000

Related U.S. Application Data

(60) Continuation of application No. 08/956,804, filed on Oct. 23, 1997, now Pat. No. 6,041,656, which is a division of application No. 08/641,374, filed on Apr. 30, 1996, now Pat. No. 5,714,787.
(60) Provisional application No. 60/007,121, filed on Oct. 31, 1995.

(51) Int. Cl.$^7$ .............................................. G01N 29/14
(52) U.S. Cl. ...................................................... 73/587
(58) Field of Search ............................ 73/587, 649, 652, 73/654, 763, 774, 778, 514.01, 514.16, 514.29, 514.34, 526, 602, 1.82; 310/328, 329, 336, 369

(56) References Cited

U.S. PATENT DOCUMENTS

| | | | |
|---|---|---|---|
| 3,566,163 A | | 2/1971 | Fischer et al. |
| 3,985,024 A | | 10/1976 | Horak |
| 4,011,472 A | | 3/1977 | Feng |
| 4,024,522 A | * | 5/1977 | Clark et al. ................... 73/587 |
| 4,036,057 A | | 7/1977 | Morais |
| 4,039,767 A | | 8/1977 | Leschek |

(List continued on next page.)

OTHER PUBLICATIONS

"Non–Destructive Characterization of Hydrogen–Embrittlemant Cracking by Acoustic Emmission Techniques": H.L. Dunegan and A.S. Tetelman; Engineering Fracture Mechanics. vol. 2., pp. 387–402 (1971).

"AE Source Orientation by Plate Wave Analysis"; Michael R. Gorman and William H. Prosser; Journal of Acoustic Emission. vol. 9, No. 4, pp. 283–288 (1991).

"Plate Wave Acoustic Emission": Michael R. Gorman; J. Acoustics Society of America (Jul. 1991).

"Relating Acoustic Emission Theory to Practice"; Michael R. Gorman; International Advances In Nondestructive Testing; Warren McGonnogle, Editor; Gordon and Breach, Publisher; vol. 17, p. 287 (1992).

(List continued on next page.)

Primary Examiner—Helen Kwok
(74) Attorney, Agent, or Firm—Knobbe, Martens, Olson & Bear, LLP

(57) ABSTRACT

A method and an apparatus for detecting and measuring cracks in plate-like structures using acoustic emission technique are disclosed. A false aperture transducer is designed to provide a criterion for filtering out extraneous noise in the acoustic emission signal based on modal analysis by computing the ratio of the high-frequency peak amplitude to low-frequency peak amplitude of the signal. A calibration curve correlating crack depth to the amplitude ratio can be obtained by simulating crack growth in a fracture specimen coupled to a test structure or field structure, and measuring acoustic emission signal in the structure by the false aperture transducer. The calibration curve correlates simulated crack depth percentage with computed peak amplitude ratio of the measured signal. Using the calibration curve and acoustic emission signal sensed by a false aperture transducer in a field structure, a crack in the structure can be detected and its depth measured by computing the peak amplitude ratio of the signal and identifying the crack depth that correlates with the ratio from the calibration curve.

5 Claims, 11 Drawing Sheets

U.S. PATENT DOCUMENTS

| | | | |
|---|---|---|---|
| 4,064,735 A | | 12/1977 | Hutchison et al. |
| 4,088,907 A | | 5/1978 | Jones et al. |
| 4,089,224 A | * | 5/1978 | Scott et al. .................. 73/587 |
| 4,353,255 A | | 10/1982 | Fukuda et al. |
| 4,535,629 A | | 8/1985 | Prine |
| 4,738,137 A | * | 4/1988 | Sugg et al. .................. 73/587 |
| 5,001,931 A | | 3/1991 | Nishimoto et al. |
| 5,029,474 A | | 7/1991 | Schulze |
| 5,101,162 A | | 3/1992 | Webster et al. |
| 5,191,558 A | | 3/1993 | Gorman et al. |
| 5,191,796 A | | 3/1993 | Kishi et al. |
| 5,251,469 A | | 10/1993 | Chan |
| 5,270,950 A | | 12/1993 | Cowley et al. |
| 5,635,643 A | | 6/1997 | Maji |
| 5,714,687 A | | 2/1998 | Dunegan |
| 5,929,315 A | * | 7/1999 | Dunegan .................. 73/587 |
| 6,041,656 A | * | 3/2000 | Dunegan .................. 73/587 |
| 6,062,083 A | * | 5/2000 | Dunegan .................. 73/587 |
| 6,173,613 B1 | * | 1/2001 | Dunegan .................. 73/587 |

OTHER PUBLICATIONS

"Experimental Far–Field Widebank Acoustic Waves in Wood Rods and Plates"; M.A. Hamstad et al.; Proceedings Of The 9th International Symposium On Nondestructive Testing of Wood; Conferences & Institutes, Washington State University (1994).

"Accurate Simulation of Acoustic Emission Sources in Composite Plates"; W.H. Prosser and M.R. Gorman; 1994 ASN"Spring Conference (1994).

"The DECI Report"; H. L. Dunegan (Jun. 1995).

"The Use of Plate Wave Analysis in Acoustic Emission Testing to Detect and Measure Crack Growth in Noisy Environments"; H.L. Dunegan; 1996 Structural Materials Technology NDE Conference (1996).

Invention Description, William H. Prosser and Michael R. Gorman, Sep. 1993.

* cited by examiner

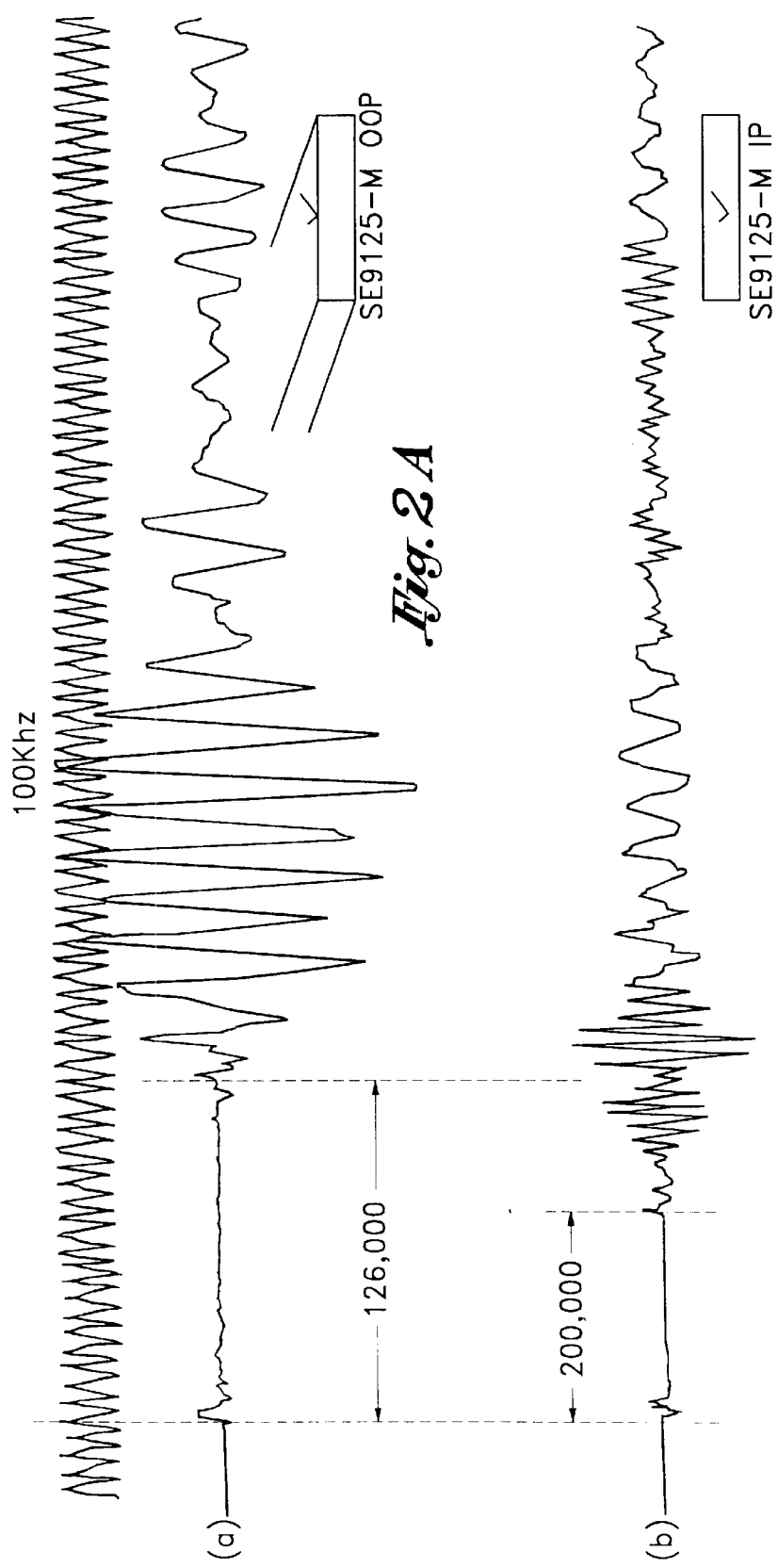

TRANSDUCER FOR MEASURING ACOUSTIC EMISSION EVENTS

RELATED APPLICATION

This application is a continuation of Ser. No. 08/956,804, filed Oct. 23, 1987, now U.S. Pat. No. 6,041,656, which is a division of Ser. No. 08/641,374, filed Apr. 30, 1996, now U.S. Pat. No. 5,714,787.

Pursuant to 35 U.S.C. §119(e), this application claims priority from the provisional application, Ser. No. 60/007121, filed on Oct. 31, 1995.

FIELD OF THE INVENTION

This invention relates to acoustic emission testing of materials and structures and more particularly to detection and measurement of crack growth in noisy environments.

BACKGROUND OF THE INVENTION

Acoustic emission is the term given to stress waves created in materials by the sudden release of energy resulting from irreversible processes such as crack growth, plastic deformation, and phase transformations in solid materials. Acoustic emission (AE) techniques have been used in the field for over 25 years for the nondestructive (NDE) testing of structures, including metal and composite pressure vessels and piping. It has also found wide application in the testing of composite man-lift booms. Currently, AE techniques are used primarily for locating cracks and potential problem areas in metal structures for pressure boundary applications, while other types of nondestructive techniques are necessary to provide acceptance or rejection criteria. The AE technology has not achieved the same level of acceptance as other nondestructive techniques for the field testing of structures such as bridges and other components of infrastructures for two primary reasons: (1) the difficulty in separating valid signals from those caused by extraneous noise, and (2) the inability of the AE techniques to determine the size of the crack or flaw.

When a crack grows in a metallic material under stress due to fatigue, stress corrosion cracking, or hydrogen embrittlement cracking, a small amount of strain energy is released in the form of a stress wave that propagates from the source of the crack at the velocity of sound in the material. The increment of time in which the strain release occurs is on the order of a microsecond or less. Thus the frequency content of the stress wave is very broad band, ranging from a few kilocycles to over 1 megacycle in frequency. In solids, two types of stress waves can exist in the bulk of the material: an extension wave, where the particle motion is parallel to the direction of propagation, and a shear wave, where the particle motion is perpendicular to the direction of propagation.

The energy of the stress wave from the crack usually consists of both an extension wave and a shear wave. Most structures constructed from metal are plate-like in nature, examples of which include pressure vessels, bridges, and aircraft. Therefore, the stress wave shortly after initiation will strike a boundary. If it strikes the boundary at an angle, Snells Law prevails and mode conversion of an extensional wave to a shear wave can occur, while a shear wave can mode-convert to an extension wave. The behavior of the stress wave can become very complicated by the time it has traveled a distance of several plate thicknesses away from the crack. In this situation, the propagating waves will be governed by Lamb's homogeneous equation, the solution to which are known as Lamb waves. In the limit where the wavelength is much larger than the plate thickness, a simpler set of governing equations derived from classical plate theory can be used to model the motion. Under classical plate theory, the waves are called plate waves, and there are two modes of propagation, namely, the extensional mode and the flexural mode. Both have in-plane (IP) motion and out-of-plane (OOP) motion. The OOP motion is the greatest for initial displacements of a source perpendicular to the plane of the plate, and the IP motion is greatest for initial displacements of a source parallel to the plane of the plate. For example, the sudden propagation of a crack will create primarily an IP wave, because the crack normally grows in a direction perpendicular to the plane of the plate, while impacts on the surface of the plate will create primarily OOP sources, since the initial source function creates a bending or flexural wave.

The stress waves (acoustic emission (AE) events) in present practice are detected by a piezoelectric transducer that is attached to the surface of the structure with vacuum grease, vaseline, or other couplants to provide an air-free path for the high frequency waves to reach the active element of the transducer. The transducer used in the majority of the tests has a resonant frequency of approximately 150 kHz. When the AE waves strike the transducer, they set it "ringing" at its resonant frequency. The use of a resonant transducer increases the sensitivity of detecting the AE events. Since the frequency contents of the waves are very broad band, they will activate the resonant frequency of any transducer having a resonant frequency between 20 kHz and 1 MHz. Most AE data is taken in the 100 to 500 kHz frequency range, where the data is low enough in frequency that attenuation effects are minimal, and high enough in frequency so that low frequency air borne noise is eliminated.

A majority of the practical AE tests are conducted on structures made from plates or plate-like components. Recent research has shown that out-of-plane (OOP) AE sources produce strong flexural wave components in a plate, with weak extensional components, while in-plane (IP) AE sources produce strong extensional waves in a plate with weak displacement components normal to the plate surface.

For many years, researchers and field test engineers employing acoustic emission techniques have used the breaking of a pencil lead on the surface of a structure or specimen to simulate the type of AE signal present when a crack propagates or when fibers break in composite structures. Because this is an OOP source, most of the energy goes into the flexural wave which is inherently low frequency, and only a small portion of the energy is carried by an extensional wave.

Michael R. Gorman, in his paper entitled "Plate Wave Acoustic Emission," Journal of Acoustic Society of America, 90(1), July 1991, used broad band sensors to detect both types of waves. By mounting the transducer on the surface of an aluminum plate, extensional waves were simulated by breaking pencil leads on the edge of the plate, and flexural waves were simulated by breaking the pencil lead on the surface of the plate. Further work by Gorman and Prosser, "AE Source Orientation by Plate Wave Analysis," Journal of Acoustic Emission, Vol. 9, No. 4 (1990), consisted of machining slots at different angles in a plate to observe the response when pencil leads are broken at an angle, which is measured from the plane of the plate. As expected, it was found that for 0 degrees, the highest signal amplitudes occurred for extensional waves, and for 90 degrees, the highest signal amplitudes occurred for flexural waves. A mixture of both waves was found for intermediate angles.

The broad band transducer used by Gorman and Prosser is problematic for a number of reasons. First, it was designed for ultrasonic testing with a resonant frequency of 3.5 MHz, and was presumed to have a flat frequency response from a few kHz to 1 MHz. However, although the measured frequency response of similar transducers yields a fairly flat frequency response from 300 kHz to 1 MKz, it is far from flat from 10 kHz to 300 kHz. In addition, its sensitivity in the frequency range below 1 MHz is an order of magnitude lower than those of resonant transducers normally used for acoustic emission testing. Consequently, the sensor must be placed close to the source in order to obtain good results. Moreover, when IP and OOP amplitudes are compared from data obtained by the transducer mounted on the surface, there is a large difference in the peak amplitudes measured from the different sources. Further, the procedure presently employed by Gorman cannot be used for crack growth measurement. Gorman merely discloses a method to digitize all signals and to attempt through visual examination and pattern recognition software to determine the amount of IP and OOP components present to make a decision regarding whether or not a signal is primarily one or the other type. Because the overwhelming number of AE signals detected in the field are extraneous noise (OOP), Gorman's method requires an enormous amount of storage for the digitized signals.

One of the major reasons AE techniques have not been widely accepted is that the techniques will not give any quantitative information concerning the size of a crack or the amount of crack growth. Currently, AE is primarily used to locate the crack by the use of multiple channels. By measuring the time that each transducer receives the AE signal, and ascertaining the velocity of sound in the material, the source location can be calculated.

The second main reason for the lack of wide application of AE techniques to monitor structures in the field is the difficulty in separating extraneous background noise from the AE signals coming from the crack. Impacts on the field structure from wind-blown sand, particles, rain, maintenance personnel, and leaks in pressurized components all can give noise signals in the frequency band of interest. Rubbing friction between components is another source of extraneous noise that has frequency components in the frequency range of interest. Most extraneous noise sources of this type are out-of-plane (OOP) sources, and although they can have very high-frequency components in an undamped structure, most of the energy in the stress waves created by such sources in most structures constructed from plates can be found at frequencies below 100 kHz. This energy is carried by a low-frequency flexural wave in the plate. AE signals generated by crack growth, on the other hand, are in-plane (IP) sources, and most of the energy in the stress wave is carried by high-frequency extensional and shear waves.

SUMMARY OF THE INVENTION

There is a need, therefore, for a method and an apparatus of eliminating extraneous noise in an AE signal and determining crack size from the AE signal.

This invention provides a solution to the above major problems encountered in current acoustic emission testing by using the ratio of the extensional wave to the flexural wave as a filter for eliminating extraneous noise and determining crack size. Special transducer and instrumentation techniques are used to recognize the type of wave predominant in a plate or plate-like structure to allow filters to be constructed in the instrumentation to not only eliminate extraneous noise sources from the AE data, but also make available nondestructive measurement of the depth of a growing crack in the structure by AE techniques. In addition, OOP signals are eliminated early on so that a smaller amount of storage is required to store the data for crack-like IP signals. The invention will be discussed in relation to crack growth in metals, but is not restricted to metals only.

In accordance with one aspect of the present invention, a false aperture transducer is formed by partially mass-loading a large crystal with a mass. The partially mass-loaded portion of the crystal reacts as a displacement-sensitive element and responds well to out-of-plane (OOP) sources, while the remainder of the crystal is sensitive to the higher frequency in-plane (IP) sources. The ratio of sensitivity to the high-frequency IP source and low-frequency OOP source can be calibrated to a specific value. The presence of an OOP signal will produce a ratio of the high-to-low frequency amplitude of lower than the sensitivity ratio of the transducer and an IP signal will produce a frequency amplitude ratio higher than the sensitivity ratio. In a preferred embodiment, the sensitivity ratio of the transducer is calibrated to be equal to one so that the transducer is equally sensitive to OOP and IP sources.

To obtain the high-to-low frequency amplitude ratio of an AE signal, a false aperture transducer is used to sense the signal. The AE signal is split into a high-frequency component and low-frequency component with analog filters and amplified. The high-frequency component is filtered with a high-pass filter, and the low-frequency component is filtered with a bandpass filter. The peak amplitudes of the two components are measured, from which the frequency amplitude ratio is calculated.

The high-to-low frequency amplitude ratio can be used to filter out extraneous noise by eliminating ratios that are lower than the calibrated sensitivity ratio of IP to OOP sources of the false aperture transducer. A portable instrument can produce an audio signal to an operator upon detecting a ratio higher than the sensitivity ratio, which indicates a crack-like IP source. Location of the crack-like source can be determined by detecting the AE signal from three different locations and ascertaining the point of intersection.

Significantly, the determination of crack size is also made possible by computing the high-to-low frequency amplitude ratio. To do so, a calibration curve correlating crack depth with the frequency amplitude ratio is obtained by cloning a fracture specimen or similar block of material onto the structure to be tested or a plate-like specimen with similar thickness. Crack growth is simulated in the fracture specimen which is attached to the structure. A false aperture transducer on the structure receives the AE signal generated and the high-to-low frequency amplitude ratio is computed. By simulating different crack depths in the fracture specimen and computing corresponding amplitude ratios from the AE signal, a calibration curve is obtained. To measure crack depth, the false aperture transducer is placed on the structure and AE signals sent to an instrumentation for computing the high-to-low frequency amplitude ratio. The corresponding crack depth can be determined with the amplitude ratio by the calibration curve. The crack profile is approximated by assuming a semi-elliptical shape.

BRIEF DESCRIPTION OF THE DRAWINGS

FIG. 7 is a block diagram of a crack measurement instrumentation illustrating another preferred embodiment of the present invention.

DETAILED DESCRIPTION OF THE PREFERRED EMBODIMENT

Figure 1:
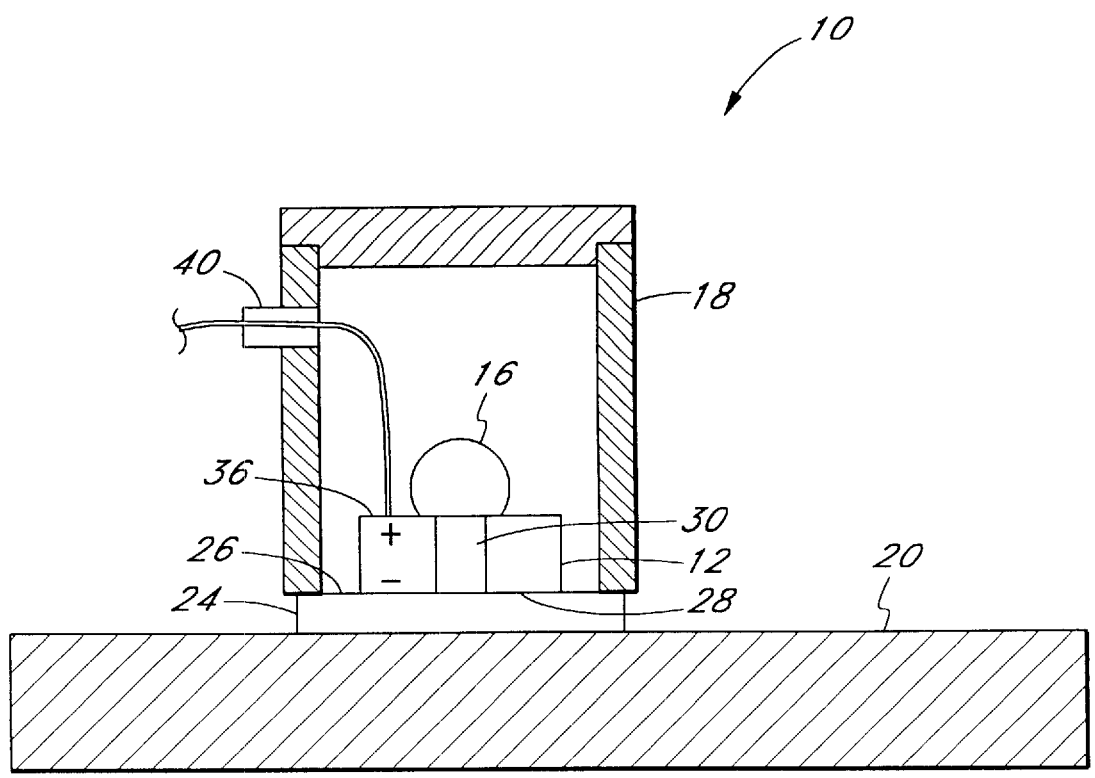
FIG. 1 is a front elevational view of a transducer illustrating a preferred embodiment of the present invention.

To filter out extraneous noise and measure crack size, a transducer 10 shown in FIG. 1 is employed. The transducer 10 responds to in-plane and out-of-plane acoustic emission signals with a particular sensitivity. Through modal analysis of the high-frequency and low-frequency components of the signal sensed by the transducer 10, a filter can be constructed to filter out extraneous noise, an instrumentation can be configured to locate a crack and measure the size of the crack.

A. Dual Purpose False Aperture Transducer

Most acoustic emission transducers respond to both OOP and IP sources and detect the presence of both modes for either of the above inputs. For filtering out noise and ease of analysis, a desirable transducer would respond to an IP source with no evidence of OOP signals and to OOP sources with no evidence of IP signals. Such a transducer can be constructed by a combination of a small aperture mass-loaded component and a larger aperture nonmass-loaded component. One embodiment is a large aperture nonmass-loaded transducer which includes a "false" small aperture created by partially mass-loading a larger crystal element. This partially mass-loaded portion of the crystal would react as a displacement-sensitive element and respond well to OOP sources, while the remainder of the crystal element would be sensitive to the higher frequency IP sources.

A preferred embodiment of the present invention is a transducer 10 comprising a piezoelectric crystal 12 that is partially mass-loaded by a mass 16 in the center, as illustrated in FIG. 1. The size of the crystal 12 and the size and size of the mass 16 are preferably selected to provide approximately equal amplitude signals for a pure OOP signal and a pure IP signal. This hybrid design advantageously achieves a balance in detection of signals, making the transducer 10 equally sensitive to both OOP and IP signals. Significantly, this facilitates the analysis of the measured data by simply examining the amplitude ratio of the two signals, as discussed below.

Referring to FIG. 1, the piezoelectric element 12 is desirably enclosed by a metal case 18. The transducer 10 is shown coupled to a structure to be tested, plate 20, with a couplant, desirably vaseline. A ceramic disk 24 advantageously provides electrical isolation between the piezoelectric element 12 and the plate 20. The top surface 26 of the ceramic disk 24 is desirably coated with a conductive epoxy in order to make electrical contact between the bottom 28 of the piezoelectric element 12 and the metal case 18. The piezoelectric element 12 in this embodiment is desirably a circular cylindrical member, desirably of about 0.5 inch and more desirably 0.5 inch in diameter, desirably about 0.15 inch and more desirably 0.150 inch in thickness, and is preferably polarized in the thickness expander mode. A hole 30 of about 0.1 inch, preferably 0.100 inch, in the center through the top surface 36 of the crystal 12 helps to broaden the frequency response. The mass 16 is desirably a ball bearing, preferably made of a tungsten carbide, which is desirably bonded to the center of the crystal 12 and partially covers the top surface 36 of the crystal. The ball bearing is desirably about 0.25 inch, more desirably 0.250 inch, in diameter, and about 0.125 inch, more desirably 0.125 inch, flat. This partial mass-loading creates a "false" aperture and makes the piezoelectric element 12 react in a displacement mode for this portion of the crystal 12. The transducer 10 is thus referred to as the false aperture transducer 10.

Breaking pencil leads on the surface of the plate 20 creates a flexure wave in the plate 20 which is low frequency in nature and gives large displacements as the wave travels past the transducer 10. Breaking pencil leads on the end of the plate 20 creates extension waves in the plate 20 with only very small displacements occurring at the surface of the plate 20 as the wave travels past the transducer 10. Mode conversions of both an extensional wave and a shear wave occur for frequency components of the AE pulse that have wavelengths smaller than the thickness of the crystal element 12. These higher frequency waves propagate into the crystal 12 and set it into resonance in areas not loaded by the mass 16. When a displacement of one of the top surface 36 or the bottom surface 28 of the crystal 12 occurs, an equal and opposite electrical charge appears on the each of the top and bottom surfaces of the crystal element 12. This electrical signal is transmitted through a connector 40 for input into other instrumentation (not shown). The inside of the case 18 is desirably filled with a polyurethane rubber compound (not shown) in order to dampen resonance of the ball bearing 16 and to provide protection against shock.

Figure 2:
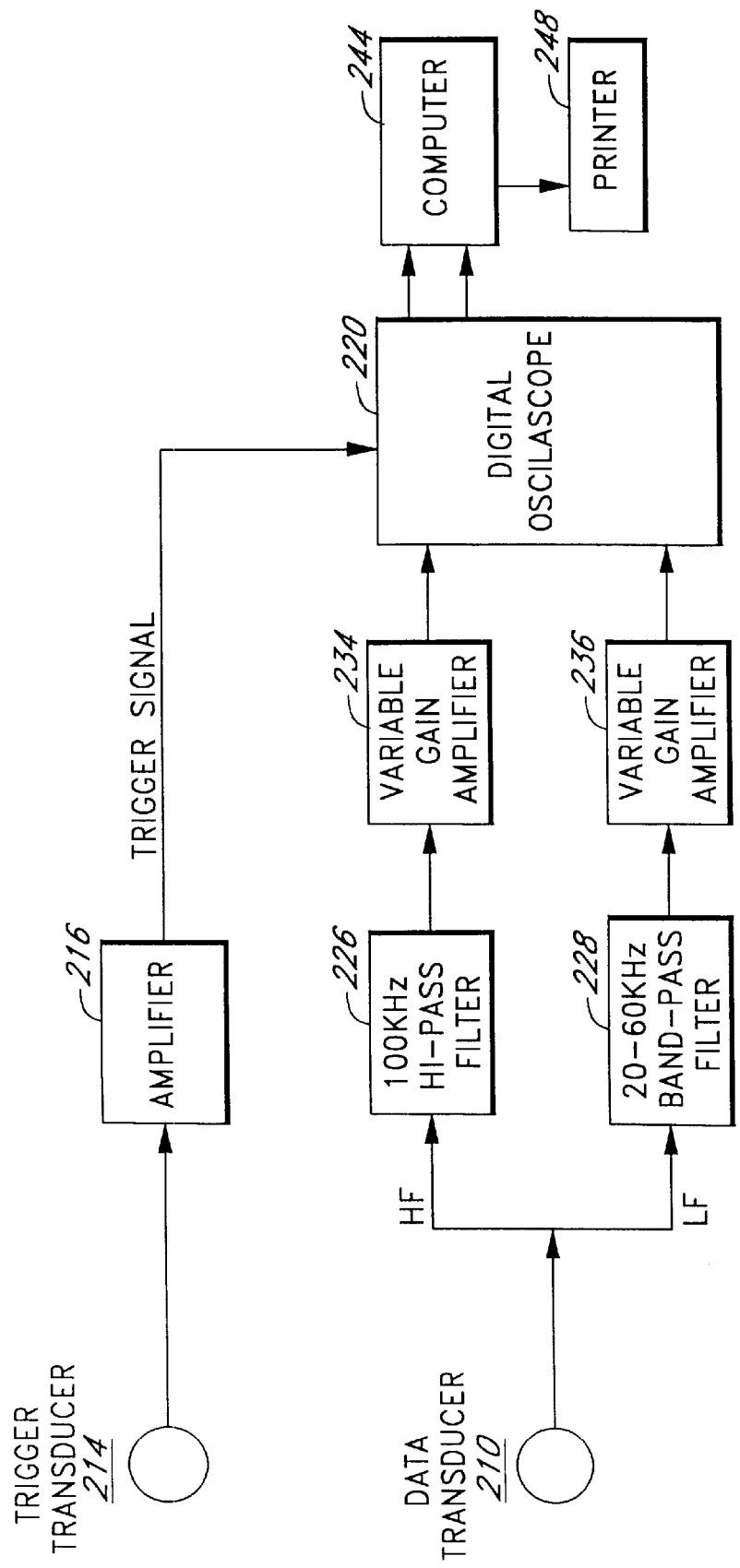
FIG. 2 is a plot illustrating the response of the transducer of FIG. 1 to out-of-plane and in-plane acoustic emission signals.

FIGS. 2a and 2b show the response of the false aperture transducer 10 to OOP and IP waves in a ½ inch thick steel plate of 48 inches in length with pencil lead breaks made at one end and the transducer 10 located at 24 inches from the end. FIG. 2a shows the response to an OOP signal, which is the type of signal that would be observed for extraneous noise, such as impact on the bar, rubbing friction, and airborne noise. FIG. 2b shows the signal from an IP source which may be created by breaking a pencil lead on the end near the mid-plane of the plate. This simulates the type of signal that is created by crack growth. Dividing the amplitude of the IP signal by the amplitude of the OOP signal gives a ratio of less than 1. Experiments have shown that the presence of an OOP signal would produce a ratio of the high-to-low frequency amplitude of much less than 1, whereas an IP signal would give a ratio of high-to-low frequency of greater than 1. As discussed below, this frequency peak amplitude ratio can be used not only to design a filter to eliminate extraneous noise, but to compute crack growth.

Other transducers can be configured to possess the characteristics of the dual component system exhibited in the false aperture transducer 10 of FIG. 1 just described. Experiments have shown that a small aperture mass-loaded transducer is the best type of transducer to use for accurately defining the displacement and frequency content of OOP sources. This type of transducer is very insensitive to IP sources which one associates with crack growth. On the other hand, a large aperture transducer without mass loading is very sensitive to IP signals and less sensitive to OOP signals. For equal sensitivity to IP and OOP signals, a desirable transducer would have a small aperture mass-loaded element with a larger nonmass-loaded element, which may be achieved by having a large piezoelectric element with a hole in the center to place the smaller mass-loaded element. The same effect can be accomplished by simply placing a small mass at the center of the large aperture element By adjusting (1) the size of the mass, (2) the relative area of the large aperture element covered by the mass, (3) the size (diameter and thickness) of the large aperture element, (4) the aperture size, and (5) the diameter of the ceramic disk, the sensitivity of the transducer to OOP and IP sources of AE signals can be adjusted so that it has equal sensitivity for both types of signals or a desirable ratio of sensitivity.

To illustrate a method of selecting a set of desirable parameters for a transducer, the experimental procedure for obtaining the parameters for the preferred embodiment of the transducer 10 of FIG. 1 is described. It is understood that this is an example to illustrate, not to restrict, the methodology. The procedure involves testing transducers having similar configuration as the transducer 10 but with different aperture sizes and mass loading for detecting plate waves. For instance, two narrow steel plates of two different thicknesses are subjected to both out-of-plane (OOP) and in-plane (IP) sources and the response of transducers having several different aperture sizes mounted on the plates are observed. The OOP source can be simulated by the breaking of a 0.3 mm 2H pencil lead on the surface at one end of the plate, and the IP source from breaking leads on the end of the plate. The transducer is desirably placed midway on the surface of the plate for both situations. Different aperture sizes can be created desirably by bonding 0.040 inch thick ceramic disks of different diameters to a crystal element in the transducer. Epoxy is desirably cast around the disks and then machined to expose the ceramic disk and provide a supporting rim to keep correct alignment during the testing. Two mild steel metal plates 48 inches long by 2 inches wide are used.

Figure 3:
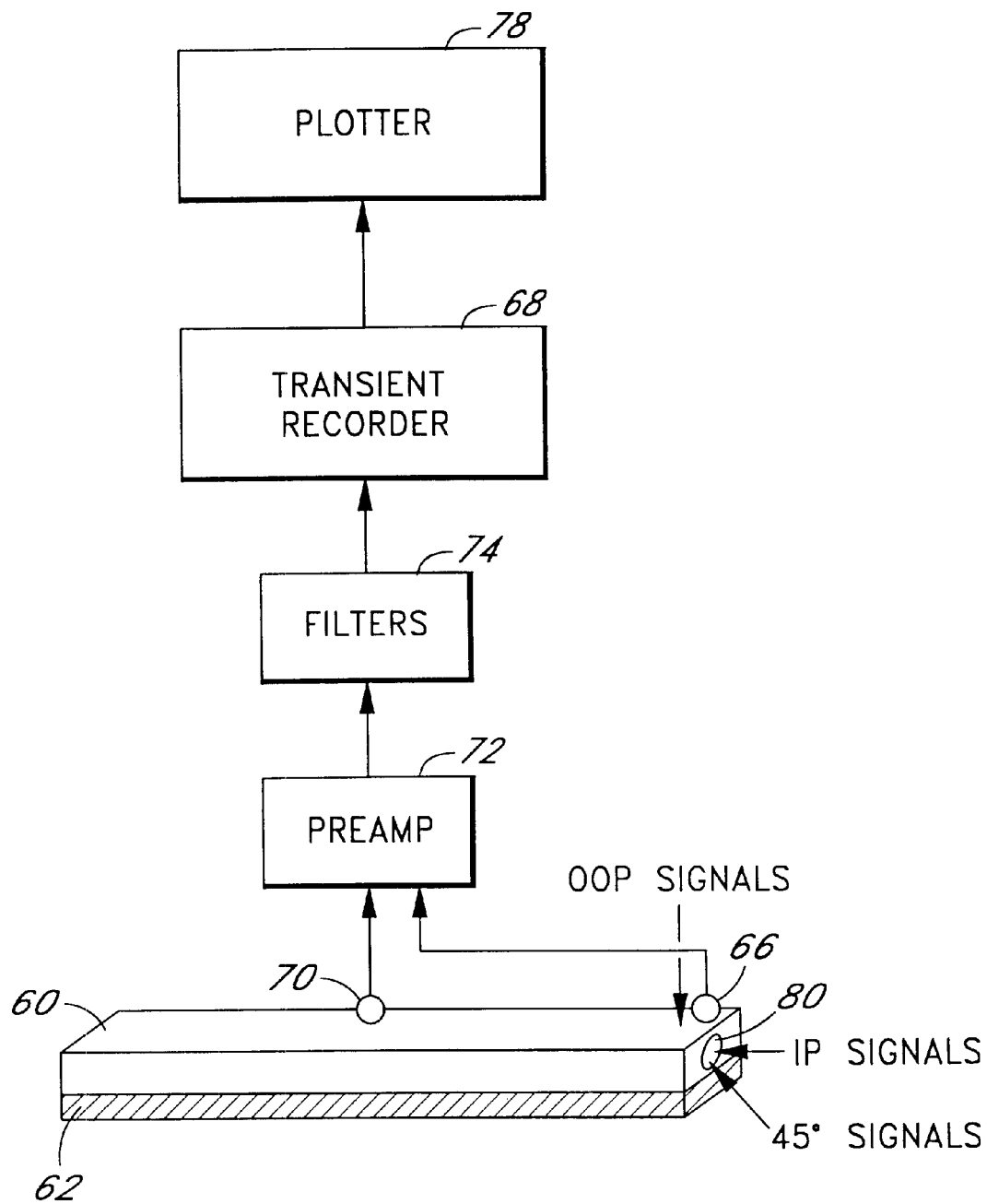
FIG. 3 is an apparatus for experimentally designing a transducer for desirable sensitivity to in-plane and out-of-plane signals.

FIG. 3 shows a schematic of the apparatus for carrying the experimental procedure. A plate 60 is used to simulate a test structure, one ¼ inch thick and the other ½ inch thick. The plate 60 is coated on the bottom surface with a damping material such as a rubber compound 62 to more closely simulate actual structures in the field. For instance, pressure vessels and piping normally have something inside that is effective in absorbing acoustic energy propagating in the wall, and most other structures have coats of paint or other materials on the surface that act to absorb energy from the plate waves generated by a crack or leak. The damped plates are designed to simulate these conditions.

A trigger transducer 66 generates a trigger signal and starts the sweep of a transient recorder 68. A data transducer 70 is coupled to the plate 60 and receives AE signal which is pre-amplified by a pre-amplifier 72. The signal is then split into high-frequency and low-frequency components that are filtered by filters 74. The components then pass through the transient recorder 68 and the result is sent to a plotter 78.

Most of the data is taken with the acoustic emission transducer placed midway along the length of the plate 60 (24 inches). A 45 degree flat bottomed hole 80 is desirably machined in one end of each plate 60. This provides the capability of breaking pencil leads at a 45 degree angle or directly on the flat portion of the hole 80 to produce an in-plane (IP) signal in the plate 60. Out-of-plane signals can be generated by breaking leads on the top of the plate 60 at one end. This setup shown in FIG. 3 may be modified for some of the experiments by positioning a ⅛ inch aperture 650 kHz transducer (not shown) at the end where the pencil leads are broken. This provides a zero time reference to the data and allows velocity measurements to be made on the various types of waves produced. The transient recorder 68 is desirably an A/D converter with a sampling rate of 20 MHz and 8 bits of resolution.

After trying several combinations of different crystal elements and masses, the transducer 10 of FIG. 1 is selected, having a 0.500-inch diameter PZT element of 0.150 inches in thickness with a 0.100-inch hole in the center as the large aperture element, and a 0.250-tungsten carbide ball bearing with an ⅛-inch diameter flat bonded in the center of as the small mass-loaded in the center of the larger aperture element. When the transducer 10 of this type is placed on the surface of the plate 20 and a wave from an OOP source travels down the plate 20 of FIG. 1, the mass-loaded center of the crystal 12 acts as a displacement device and gives a large amplitude signal from this OOP source. When an extensional wave is present in the plate 20 from an IP source, very little displacement occurs at the surface, but mode conversions from the extensional wave occurs and starts the larger aperture element 12 to "ring" at its resonant frequency. A signal for these types of waves traveling at the shear velocity in the material is also observed.

Although a transducer that is equally sensitive to both OOP and IP signals is desirable in practice, as discussed in its application below, it may be advantageous for a transducer to be more sensitive to one of the two types of signals in some situations. For instance, a small specimen produces a lot of high frequency signals from reflection within the boundary of the specimen during testing. A transducer that is more sensitive to OOP signals than to IP signals would be more appropriate and effective for acquiring data in a small specimen. An example is a transducer that has an enhanced response to OOP signals, comprising a piezoelectric element of ⅛ inch in diameter and 0.05 inch in thickness mass-loaded by a tungsten carbide ball bearing of ¼ inch in diameter and having an ⅛ inch flat.

As long as the ratio of the sensitivity of a transducer to OOP and IP signals is known, the transducer can be used to filter out extraneous noise and measure crack growth via modal analysis, as discussed in detail below. The construction of an AE transducer can thus be tailored to the specific structure and application. It is thus contemplated that a transducer that is configured and calibrated for a specific sensitivity to OOP and IP signals in acoustic emission testing would fall within the scope of this invention.

B. Filtering Out Extraneous Noise

The first application of the modal analysis of the OOP and IP signals is filtering out extraneous noise. Noise in an acoustic emission test, such as impact of particles due to rain and dust, and noise due to friction, are primarily OOP sources. AE signals due to crack growth in metals and other materials, and fiber breakage in composites, are IP sources. The requirement that an AE signal be an in-plane (IP) signal is the first criteria for acceptance of the AE data. Eliminating the noise early in the data gathering process will make analysis of crack-like signals much easier. The only IP signal that could be considered extraneous noise would be due to crushing of oxides on the crack surface at minimum loads from a crack undergoing cyclic loading. Furthermore, signals having strong OOP components could be eliminated early in the data gathering process in order to eliminate the mass storage problems and data analysis of hundreds of thousands of signals in some cases.

If a transducer can recognize which type of source is present, a front end filter can be set up, such that only signals that can be recognized as IP sources are accepted. For instance, one may split the AE signal from the transducer of FIG. 1 into high and low frequency bands, subject them to a 20–60 kHz (or 20–80 kHz) bandpass filter and a 100 kHz high-pass filter, measure their peak amplitudes respectively, and then divide the high-frequency signal by the low-frequency signal. If the ratio is greater than 1, the high-frequency signal is accepted as coming from crack growth. The ratio for acceptance can be set based on designing a plate having the same thickness of the structure to be tested.

Figure 4:
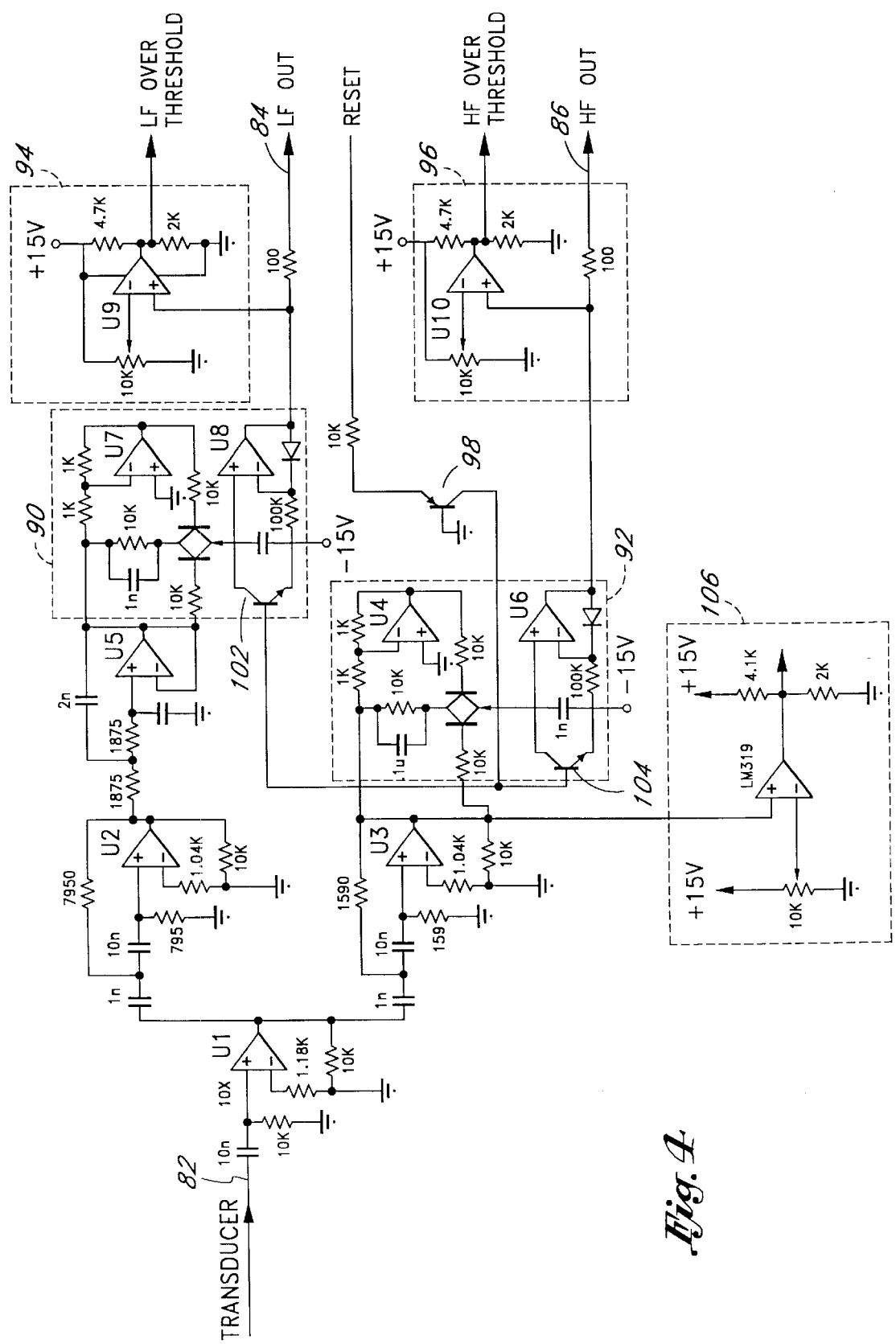
FIG. 4 is a schematic view of a circuit for filtering extraneous noise in an acoustic emission signal.

An embodiment of a circuit for carrying out the filtering function is illustrated in FIG. 4. As shown in FIG. 4, a multiple-stage, active filtering circuit includes a plurality of operational amplifiers U1-U10. Each of the operational amplifiers U1–U3 advantageously comprises OP37 operational amplifiers. U4 advantageously comprises an OP27 operational amplifier. Each of the operational amplifiers U5–U8 advantageously comprises TL071 or equivalent operational amplifiers. U9 and U10 each desirably comprises an LM319 or equivalent operational amplifier. Each of the operational amplifiers U1–U10 is powered using a ±15 volt source. The values of the various circuit components for one advantageous embodiment of the filtering circuit are as depicted in FIG. 4, although it will be appreciated by one of ordinary skill in the art that a variety of other particular circuit configurations might be used to implement the filtering operation provided by the circuit of FIG. 4.

In operation, the circuit of FIG. 4 takes the signals from the false aperture transducer at an input terminal 82, amplifies it by 40 dB, and splits it into 2 frequency bands which are output on terminals 84, 86. The low frequency band spans 20–60 kHz, the high band spans 100 kHz to several MHZ. The output of each frequency band is full-wave rectified and sent to a track-and-hold circuit which tracks the rectifier output and holds the peak value. The track-and-hold output goes to a threshold detector with an adjustable setting. A logic high is generated if the threshold is crossed. A reset input allows the track-and-hold circuits to be reset.

The output of the false aperture transducer is capacitively coupled to the amplifier U1 (together with its associated bias circuitry) having a gain of approximately 10. The output of U1 feeds two channels: the low-frequency channel above and the high-frequency channel below.

The low-frequency channel is made up of a 20 kHz 2-pole high-pass filter, followed by a 60 kHz 2-pole low-pass filter. Thus, a net bandpass filter is created by the cooperation of the low and high pass filters. The high-pass filter comprises U2 and associated components, while the low-pass filter comprises U5 and associated components. In one desirably embodiment, the high-pass filter has a gain of 10, while the low-pass filter a gain of 1.

The high-frequency channel is defined as a 100 kHz, 2-pole, high-pass filter with a gain of 10. The high-pass filter used to define the high-frequency channel comprises the operational amplifier U3 and its associated components.

The rectifiers, track-and-hold circuits, and threshold detectors for the two channels are identical. In particular, the rectifier and track-and-hold circuit for the low frequency channel are shown to be enclosed in dashed lines as the circuit 90 (including inverter U7 and buffer U8), while the rectifier and track-and-hold circuit for the high frequency channel are shown to be enclosed in dashed lines as the circuit 92 (including inverter U4 and buffer U6). In like manner, the threshold detector for the low-frequency channel is shown to be enclosed within dashed lines and designated by the reference numeral 94 (including differential amplifier U9), while the threshold detector for the high-frequency channel is shown to be enclosed within dashed lines and designated by the reference numeral 96 (including differential amplifier U10).

The basic track-and-hold circuit is configured as an emitter followed with a capacitor, instead of a resistor, as its load. The emitter follower can charge the capacitor, but not discharge it, so the emitter follower circuit acts like an electrical ratchet (i.e., where energy is input but not released). The voltage on the capacitor follows the input voltage up and holds the peak value. To make this a full-wave circuit so that it follows both positive and negative peaks, two emitter following transistors are used (shown in a "face-to-face" configuration), both connected to the same capacitor. The input of the second emitter follower is the output of a unity gain inverter. In the low-frequency channel, the inverter is U7, and in the high-frequency channel, it is U4.

Each of the two hold capacitors is shunted by an NPN transistor which discharges its associated capacitor when turned on by a reset signal. The reset signal is a logic high provided externally. That signal turns on a grounded-base PNP transistor 98 that turns on NPN transistors 102, 104. The 10 k resistors in the emitter follower base and collector circuits limit the currents to safe values when the NPNs are on. The collector resistors are bypassed by 0.1 uF capacitors to provide the brief surges of high current required to track the signal. In an advantageous embodiment, all NPN transistors are 2N3904 transistors and the PNP transistor is either a 2N3906 or 2N4403 transistor.

The output of each track-and-hold circuit is buffered by a unity gain amplifier with a diode in its feedback to compensate for the Vbe offset of the track-and-hold circuit. The buffer is U8 for the low-frequency channel and U6 for the high-frequency channel. The buffer outputs are brought out so they can be digitized by external equipment, and also are input to a pair of threshold detectors.

The threshold detector for the low-frequency channel comprises U9, while the threshold detector for the high-frequency channel comprises U10. Thus, a dual comparator configuration is defined. The reference input of the detectors are potentiometers connected across the positive supply so that the threshold can be set by the user. The comparator outputs provide a logic high when the threshold is crossed. With proper software, the user can define an event by either of the two threshold crossings, or by both.

The circuit 106 (shown at the bottom of FIG. 4) provides TTL outputs to a counter to provide "ring-down" counts for data analysis. In one embodiment, the outputs of this circuit are designed to interface with a PC-LPM-16 data acquisition board from National Instruments (not shown). Two channels of A/D (for the low and high frequency peak amplitude values), two channels of digital input (for the low and high frequency threshold crossings), one digital output (for reset), one timer (to establish a delay between sensing a threshold crossing and reading the peaks) and one counter (to accumulate threshold crossing counts) comprise the data stream for the circuit and DAQ board (not shown).

For filtering purposes, software for the computer calculates the high-to-low frequency amplitude ratio, and compares this ratio to a value input by the user (this value established by tests on a plate of comparable thickness to show the ratio of OOP to IP sources). If the voltage ratio exceeds this value, the ring-down counts will be accepted from the high frequency channel. If the voltage ratio is lower than this value, the AE counts data is not accepted, since the signal will be an OOP signal, which comprises extraneous noise.

C. Locating a Crack-Like Source

Figure 5:
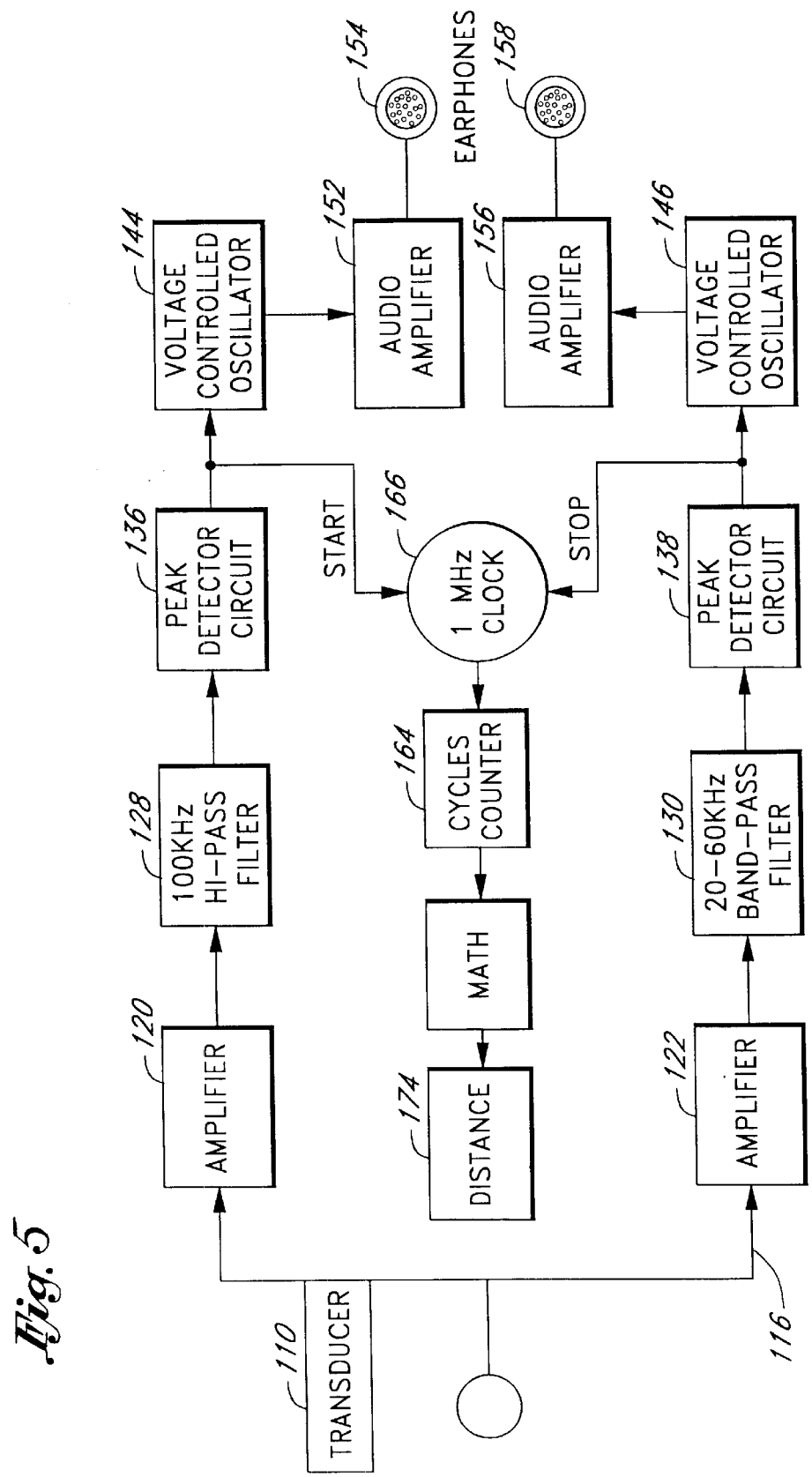
FIG. 5 is a block diagram of an instrumentation for locating a crack-like source in a structure illustrating another preferred embodiment of the present invention.

The transducer 10 of FIG. 1 can be used to locate a crack-like source. A preferred embodiment of an instrument incorporating the transducer 10 is a unit that is desirably portable, making it suitable for bridge testing and other field measurements. FIG. 5 is a block diagram of the instrument. The block diagram indicates how the difference in extraneous noise and crack-like signals can be determined with a portable system and audio earphones.

Referring to FIG. 5, the AE signal is detected by a transducer 110 and the signal is split into the high frequency channel 114 and low frequency channel 116 shown. An amplifier 120 amplifies the high-frequency signal, which then passes through a high-pass filter 128 which is desirably a 100 kHz filter. The low-frequency signal is amplified by the amplifier 122 and filtered by a band pass filter 130 which is desirably 20–60 kHz. A peak detector circuit 136 determines the high-frequency peak amplitude/voltage of the high-frequency component, and a peak detector circuit 138 determines the low-frequency peak amplitude voltage. An alternative embodiment may replace the two amplifiers 120 and 122 by a single amplifier (not shown) which amplifies the AE signal prior to splitting of the signal into high-frequency (HF) and low-frequency (LF) components. Such an embodiment is most appropriate for the transducer 10 which is equally sensitive to OOP and IP signals. The circuit of FIG. 4 may be used to perform the steps just described to obtain high-frequency and low-frequency peak amplitudes.

The low-frequency and high-frequency amplitudes are used to filter out extraneous noise and locate the crack. In one embodiment, an audio system is employed to indicate the presence of a crack-like signal. As shown in FIG. 5, the high-frequency peak voltage is then applied to a first voltage-controlled oscillator 144 which will generate a 3 second tone dependent on the peak voltage. A second voltage-controlled oscillator 146 generates a 3-second tone from the low-frequency peak voltage. A first audio amplifier 152 amplifies the high-frequency tone and applies it to an earphone 154 worn by the operator. A second audio amplifier 156 amplifies the low-frequency tone which is then fed to another earphone 158. Assuming that the high-frequency channel goes to the right earphone 154 and the low-frequency channel goes to the left earphone 158, all the operator needs to observe is whether or not the right earphone 154 has a higher pitch than the left earphone 155. If the right earphone 154 does have a higher pitch, the signal detected is an IP signal and is more than likely coming from crack growth. To use the portable testing unit, one would carry the instrument in a battery operated configuration, and wear a pair of earphones plugged into the instrument to search for AE signals that can be identified as coming from a crack-like source, as opposed to extraneous noise.

Alternatively, the two peak voltages from the high-frequency and low-frequency channels may be compared to determine whether the analog, high-to-low frequency peak amplitude ratio is greater than 1 (not shown). If the ratio is greater than 1, a tone is generated and audio-amplified. The operator can thus identify the tone as indicating detection of a crack.

In situations where the transducer 110 is not calibrated to be equally sensitive to OOP and IP signals, the amplification of each channel can be varied independently by calibrating the amplifiers 120 and 122 to adjust the peak voltage in each channel such that a high-to-low frequency peak amplitude ratio of one or less corresponds to an OOP signal as determined in the calibration sequence on the particular structure under test. In this manner, the dynamic range of the tones generated in each channel will be calibrated. For example, a 440 A tone may be set to correspond to a ratio of one with a dynamic range of one octave higher and lower than 440 to cover a specified range of voltage ratios.

Figure 6:
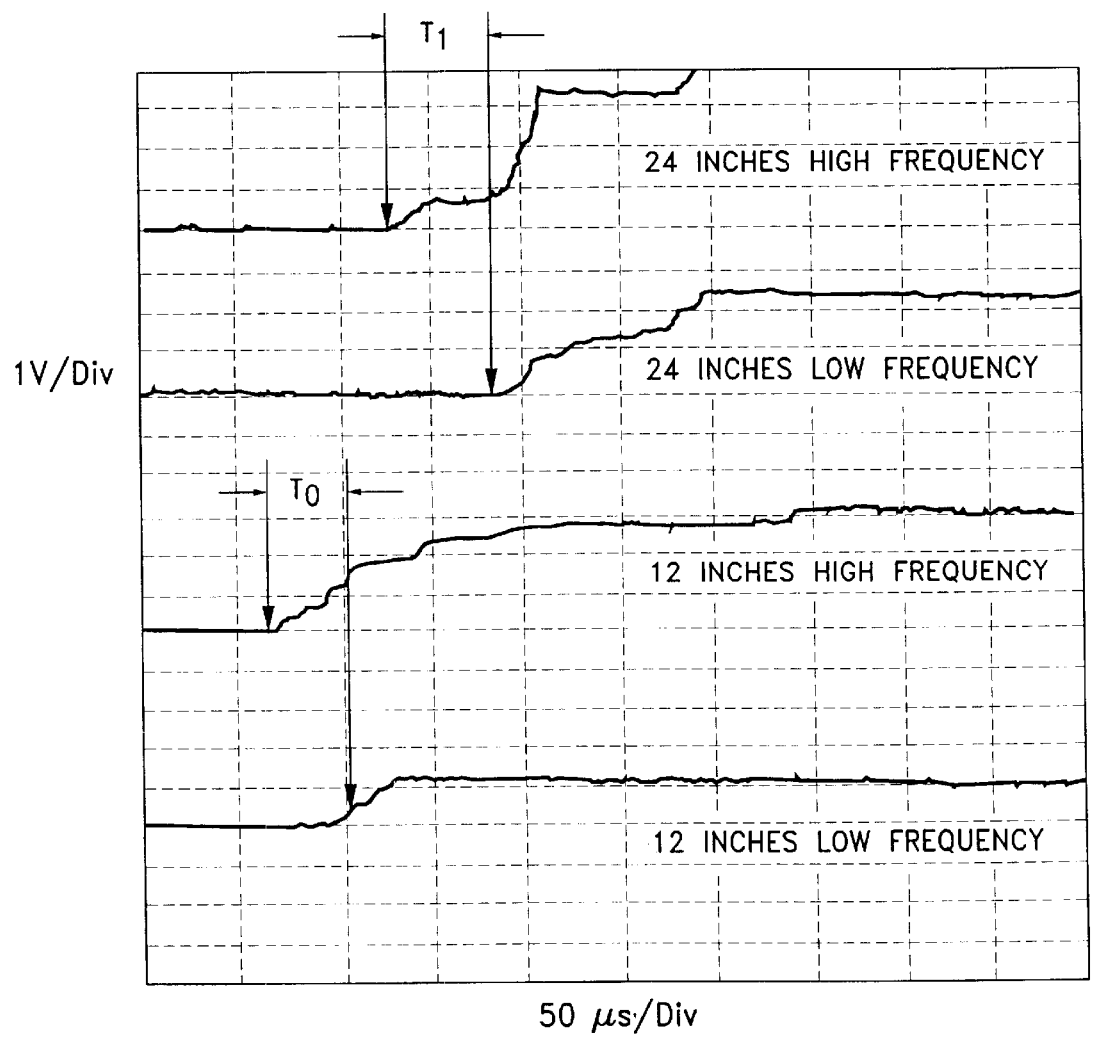
FIG. 6 is a graph of peak detected signals from the transducer of FIG. 1 obtained with the instrumentation of FIG. 5.

If the operator determines that a crack-like source is within the range of the instrument, the location of the source can be found as follows. Because the velocity of the extensional wave is the highest and nondispersive, and the leading edge of the low-frequency dispersive wave arrives at the shear velocity, the time difference between the two signals will vary as a function of the distance of the source from the transducer 110. An example is illustrated in FIG. 6, which shows the output of the peak detection circuit 136 for the high-frequency channel 114 and the peak detection circuit 138 for the low-frequency channel 116 when the false aperture transducer 10 of FIG. 1 is placed at 12 inches and 24 inches distance from the end of a ½ inch thick steel plate. 0.3 mm pencil lead breaks are made at 25% depth at the end of the plate to produce the signals shown in FIG. 6. The time difference between the high and low frequency signals represented by $T_0$ and $T_1$ in FIG. 6 varies as a function of the distance of the transducer 110 from the source. This time difference can be calculated from the known velocities of the waves in the plate in the following manner:

Let $T_e$ equal the time required for an extensional wave to travel a distance D at a velocity $V_e$, then $$T_e = D/V_e \tag{1}$$

and $T_s = D/N_s$ is the time required for a wave traveling at the shear velocity to cover the same distance D. The difference is $$T_s - T_e = D(1/V_s - 1/V_e) = T_0 \text{ or } T_1 \text{ in FIG. 6} \tag{2}$$

For steel:

$$V_e = 2.13 \times 10^5 \text{ in/sec and } V = 1.23 \times 10^5 \text{ in/sec} \tag{3}$$

From (2) and (3)

$$T_s - T_e = D(3.44 \times 10^{-6}) \tag{4}$$

$$D = (T_s - T_e)/3.44 \times 10^{-6} \tag{5}$$

In the example illustrated in FIG. 6, the calculated values for $T_0$ and $T_1$ (Equation 4) are:

$T_0 = 12(3.44 \times 10^{-6}) = 41$ microseconds and
$T_1 = 24(3.44 \times 10^{-6}) = 83$ microseconds.

The measured data in FIG. 6 correlates well with these values. The distance D can thus be solved in accordance with Equation (5).

Referring to FIG. 5, if the threshold detection of the high frequency channel 114 is used to start the cycle counter 164 in counting the cycles of a 1 MHz clock 166, and the threshold detection of the low frequency channel 116 is used to stop the cycle counter 164, the number of cycles counted will correspond to the number of microseconds delay between the extensional wave and lower frequency flexural wave. One can then solve for the distance 174 from the transducer to the source by Equation 4 above. This distance 174 corresponds to the radius of a circle D, and the source is located somewhere on this circle. If one moves the transducer 110 a known distance twice and again makes the same time measurements and calculations, the source corresponds to the intersection of the three vectors defined.

In yet another embodiment (not shown), the 1 MHz clock 166 and cycle counter 164 are used to output the peak detected signals to a portable digital oscilloscope (not shown) and to capture the signals and make a visual measurement of the time differences. This method can be used to generate the signals in FIG. 6. The time difference can be used to compute the distance D according to Equation (5).

D. Measuring Crack Size

Crack growth in a structure or specimen predominantly occurs normal to the plane of the plate carrying a tension load. The incremental extension of the crack due to events such as fatigue, stress corrosion cracking, and hydrogen embrittlement, becomes an IP source for acoustic emission signals, which can be simulated by the breaking of a pencil lead on the edge of a structure at different depths along the thickness of the structure. Signals originating from these IP sources produce different types of signals. There is an increasing amount of flexural waves for crack growth nearing the surface as compared with crack growth at midthickness. For example, if during a fatigue test of a specimen with a thumbnail surface crack, one observes a decreasing amount of flexural wave component in the AE signal as the crack grows, this would be indicative of a crack having a depth less than half the distance through the plate. On the other hand, if one observes an increasing amount of flexural component as the crack grows, this would be an indication that the crack is deeper than one-half the thickness of the plate. However, the amplitude of the high-frequency extensional wave remains unchanged. Its amplitude is independent of where the pencil lead is broken along the thickness. This is an important phenomenon and is the key to keeping the ratios of the two frequencies independent of the absolute amplitude of the initial detected signal.

The crack depth can be defined in more detail by correlating it with the ratio of the high-to-low frequency components of the signals from a transducer in accordance with the present invention. The ratio of the high-frequency to lowfrequency amplitudes can be correlated to determine where in-the depth of a structure that a real crack is propagating, regardless of the amplitude of the signal created by the incremental crack growth, since the amount of flexure wave created should only be a function of the moment around the neutral axis and not the amplitude. The ratio increases as a surface crack grows in depth of a plate or plate-like structure, reaches a maximum at mid-thickness, and decreases as the crack grows deeper.

This correlation forms a set of data that could then be used in the field on structures constructed from plates or plate-like components of the same material to estimate crack depth. The calibration plates and structures do not need to have the same thickness because the correlation is based on percentage depth. Cracks do not usually grow by extension across the whole crack front, especially in thicker plates. Rather, surface cracks generally grow in a semi-elliptical shape. Therefore, careful measurement of signal mode ratios (highto-low frequency amplitude ratios) will allow one to determine not only the maximum depth of the crack, but also the profile or shape of the crack.

For all cracks, including through cracks, the acoustic emission counts can be used to estimate the amount of crack growth, and the voltage ratios will be used primarily as a filter to eliminate extraneous OOP sources of AE signals. See H. L. Dunegan & A. S. Tetelman, "Non-Destructive Characterization of Hydrogen-Embrittlement Cacking by Acoustic Emission Techniques," Engineering Fracture Mechanics, Vol. 2, pp. 387–402 (1971), which is hereby incorporated by reference.

An instrumentation for detecting crack size and crack growth in a structure is illustrated in the block diagram of FIG. 7. A data transducer 210 is coupled to the structure (not shown) to be examined. A trigger transducer 214 generates a trigger signal through an amplifier 216 and starts the sweep of a digital oscilloscope or voltmeter 220. The signal from the data transducer 210 is split into a high-frequency (HF) component and a low-frequency (LF) component. The 100 kHz high-pass filter 226 filters the high-frequency component, and the 20–60 kHz bandpass filter 228 filters the low-frequency component. Variable gain amplifiers 234 and 236 are used to amplify the two components, which are then input into the digital oscilloscope or voltmeter 220. The digital oscilloscope 220 captures the transient signals and passes them to the computer 244, desirably through a fiber optic cable (not shown). A printer 248 prints the waveforms. When a signal is detected or simulated, such as by breaking a pencil lead at a given depth, both the high frequency and low frequency waveforms are captured and printed.

1. Calibration

In order to predict crack depth and growth from acoustic emission signals, a calibration curve illustrating crack depth as a function of the ratio of the high-to-low frequency components of the AE signals is desirably employed. To obtain a calibration curve, the first step is to couple a fracture specimen or similar block of metal as mentioned previously to the structure to be tested.

An in-plane acoustic emission signal is then simulated in the fracture specimen to simulate crack growth with 0.3 mm Pentil pencil leads. This is repeated at different depths of the specimen. The resulting acoustic emission signal in the structure is detected by the false aperture transducer. From the signal in the structure, the ratio of the high-to-low frequency components (HF/LF) is computed for each simulated crack depth. Signals from extraneous noise sources indicated by a frequency peak amplitude ratio of less than 1 is eliminated, provided that the signal measurement of the structure is performed with a transducer calibrated for equal sensitivity to in-plane (IP) and out-of-plane (OOP) signals, such as the false aperture transducer 10 of FIG. 1. A calibration curve is then plotted for the HF/LF ratio versus crack depth, and is used to correlate frequency peak amplitude ratio with crack depth and to separate IP from OOP signals.

Figure 8:
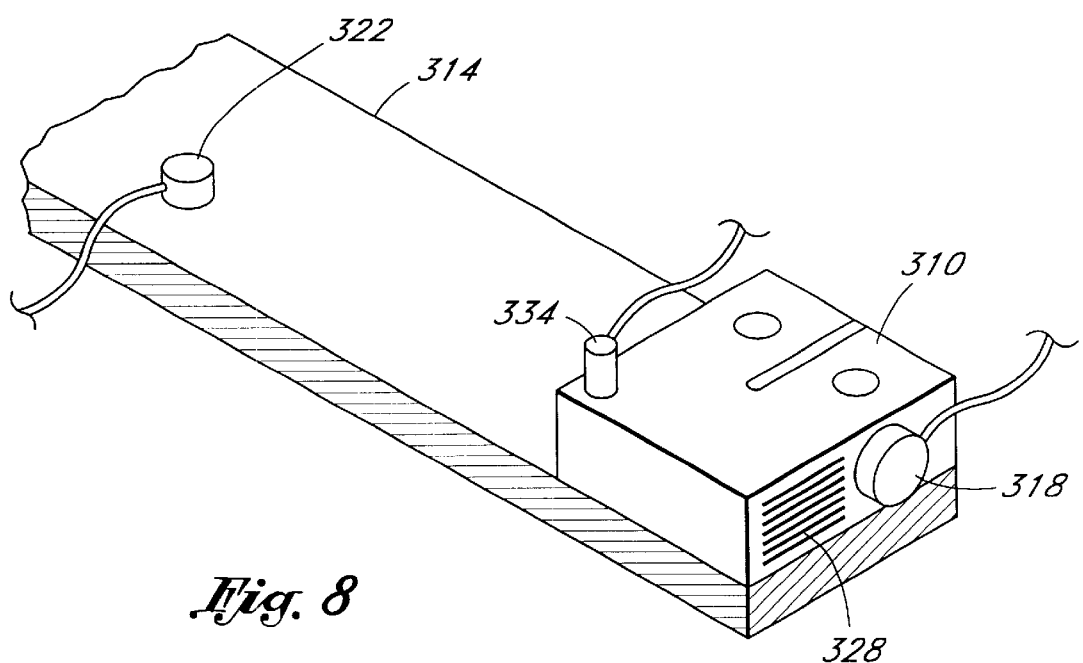
FIG. 8 is an apparatus for calibrating the instrumentation of FIG. 7.
Figure 9A:
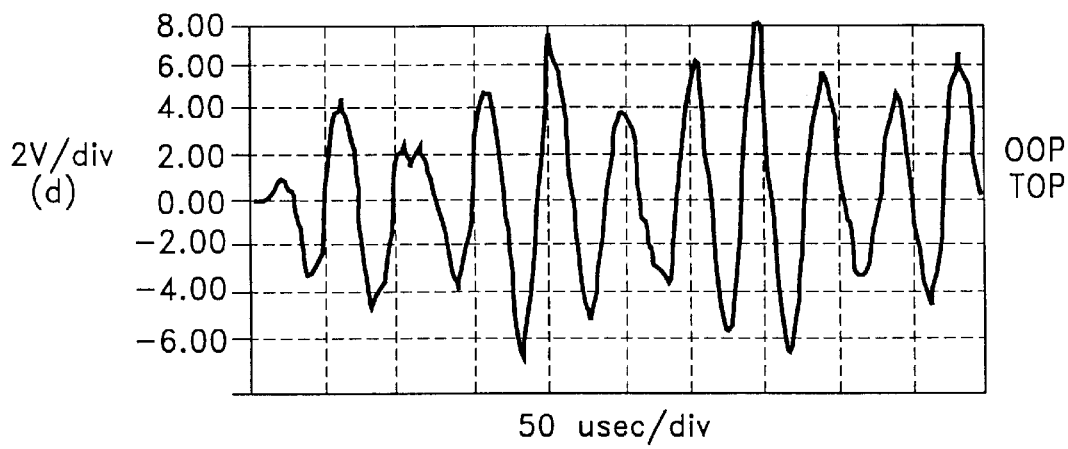
FIG. 9 is a graph showing the low-frequency data from the specimen transducer of FIG. 8.
Figure 9B:
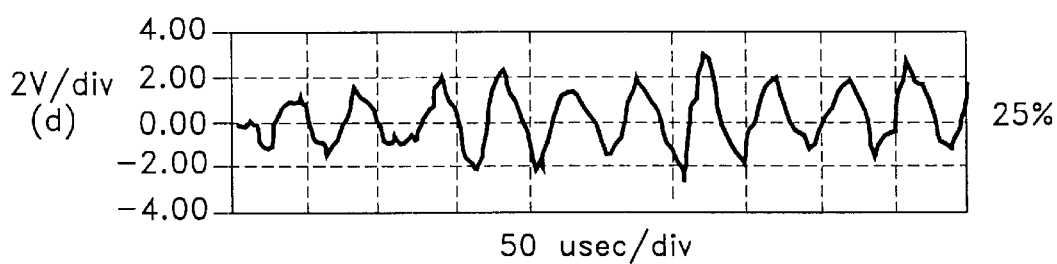
Figure 9C:
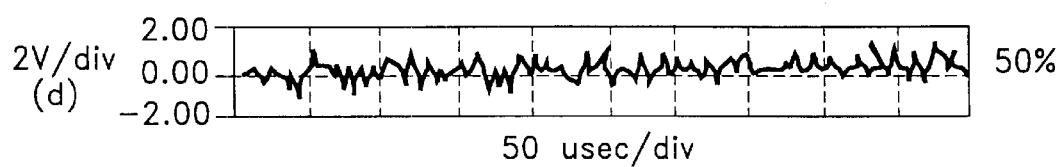
Figure 9D:
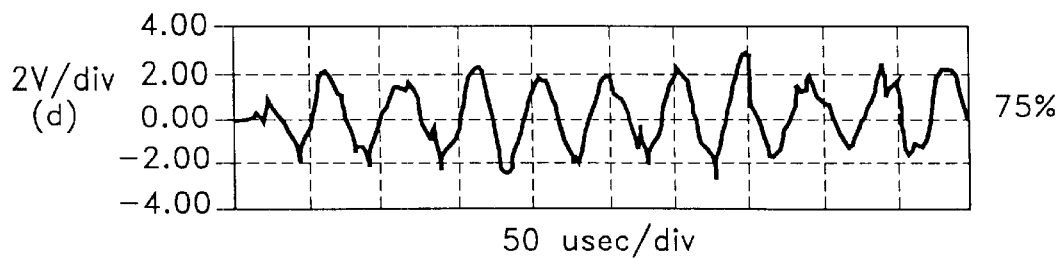
Figure 9E:
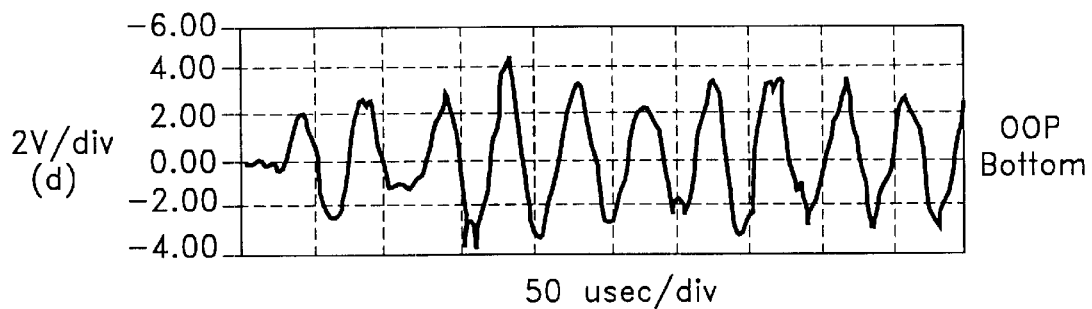
Figure 9F:
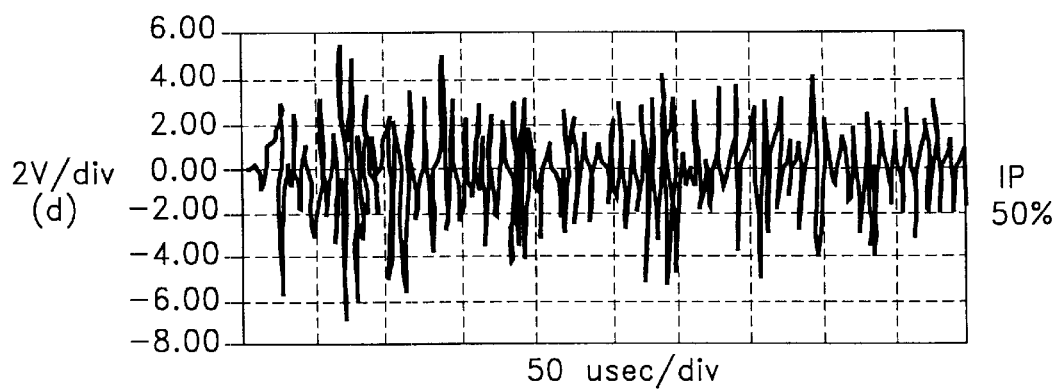

To illustrate the calibration procedure in a laboratory, an example is given as follows. For application to bridges and other thick-plate structures, steel plates of ¼- and ¾-inch thickness are suitable calibration plates. FIG. 8 shows the apparatus incorporating a ¾-inch thick compact-tension (CT) fracture toughness specimen. The CT specimen 310 is coupled to a plate 314 and a trigger transducer 318 is placed on the CT specimen 310. A data transducer 322 is disposed on the plate 314, desirably at 24 inches away. The trigger transducer 318 on the edge of the plate 314 is used to provide a trigger signal for the digital voltmeter such as the one shown in FIG. 7, voltmeter 22, when 0.3 mm Pentil pencil lead breaks are made at different depths in the specimen 310 shown by the parallel lines 328 on the edge of the specimen 310. The pencil lead breaks are desirably made at each level of the parallel lines 328. Another transducer 334 shown is desirably used to detect the AE data from the specimens 310 for each lead break. Signals in the plate 314 are recorded by the data transducer 322, which is desirably a false aperture transducer such as the transducer 10 of FIG. 1. The trigger transducer 318 is used so that velocity of sound for the different waves can be measured and phase shift of the signals can be observed. The trigger transducer 318 is desirably a small 650 kHz transducer used to provide the capability of making velocity measurements of the various types of waves produced in the narrow plate 314.

The specimen transducer 334 desirably has an ⅛-inch aperture with the piezoelectric crystal mass loaded. The aperture and size of the mass is desirably adjusted so that the transducer 334 is equally sensitive to OOP and IP signals in the specimen 310. The out-of-plane (OOP) signal may be generated by breaking the pencil lead on the top or bottom surface. The transducers 318 and 334 are desirably attached to the CT specimen 310 with hot glue.

The CT specimen 310 is coupled to the plate 314. Vaseline is desirably used to couple the CT specimen 310 to the end of the ½×3×42-inch long steel plate 314. The data transducer 322 is desirably coupled to the plate 314 with vaseline, desirably at a distance of 24 inches from the end of the plate 314. 0.3 mm pencil leads may be broken on the CT specimen 310 at different depths signified by the horizontal lines 328 on the specimen 310 as in the previous experiment, as shown in FIG. 8.

FIG. 9 shows the low-frequency data from the specimen transducer 344 on the CT specimen 310 for an OOP signal (a), and IP signals from 25% (b), 50% (c), and 75% (d) depth in the CT specimen 310. An OOP signal from the bottom surface of the specimen 310 is also shown (e). The high-frequency signals change very little as a function of depth, and hence only the signal from the 50% (f) depth is shown.

In order to provide a calibration of structure in this matter, one needs to be assured that the data recorded is representative of what one would obtain on the structure alone. The CT specimen 310 is hence removed and the trigger transducer 318 attached to the end of the plate 314 with hot glue. Pencil leads may be broken at the same percentage depth in the plate 314 as is used for the CT specimen 310 with the data transducer 322 at 24 inches from the end of the plate 314.

As shown in FIG. 7, the trigger transducer 214 represents the trigger transducer 318 of FIG. 8 and starts the sweep of the digital oscilloscope 220. The signal from the data transducer 322, represented in FIG. 7 as 210, is split into a high-frequency (HF) component and a low-frequency (LF) component. The high-frequency (HF) component is passed through the 100 kHz high-pass filter 226, and the low-frequency (LF) component through the 20–60 kHz bandpass filter 228. Each component is amplified by a variable gain amplifier 234 or 236 and then input into a digital voltmeter 220. The digital osciloscope 220 captures the transient signals and passes them to the computer, and the waveforms are then printed.

Referring to FIG. 8, the breaking of pencil leads at different depths in the CT specimen 310 unexpectedly produces dramatic changes in signal level of the low-frequency (LF) channel, even for such a thick structure which is substantially thicker than a thin plate. An OOP source results in a large low-frequency flexure-type wave being set up in the specimen 310. Lead breaks at different depths on the edge of the specimen 310 result in very little low-frequency signal at the point of symmetry at the mid-plane of the specimen 310 with increasing amounts of low-frequency signal at 25% and 75% for unsymmetrical input of the lead break. A phase shift is observed in the signals between depth levels on opposite sides from the mid-plane.

Experiment demonstrates that the response of the CT specimen 310 to lead breaks at different depths can be "cloned" into the plate 314. This is illustrated by the large flexure wave signal generated by the lead break on the top surface, compared to the very small flexure wave signal observed from the lead break made at the mid-plane of the CT specimen 310. The signals arriving at approximately 120 microseconds correlate well with the extensional wave velocity of 200,000 in/sec (5,000 M/sec) in steel. The first large signal has an arrival time corresponding to the shear velocity of approximately 130,000 in/sec (3,300 M/sec). The measured velocities of 200,000 in/sec and 131,000 in/sec correspond to the extensional and shear velocity of sound in steel. The velocity calculations may be made using the 10 microsecond markers from the 100 kHz sine wave that may also be recorded with the data.

Figure 10:
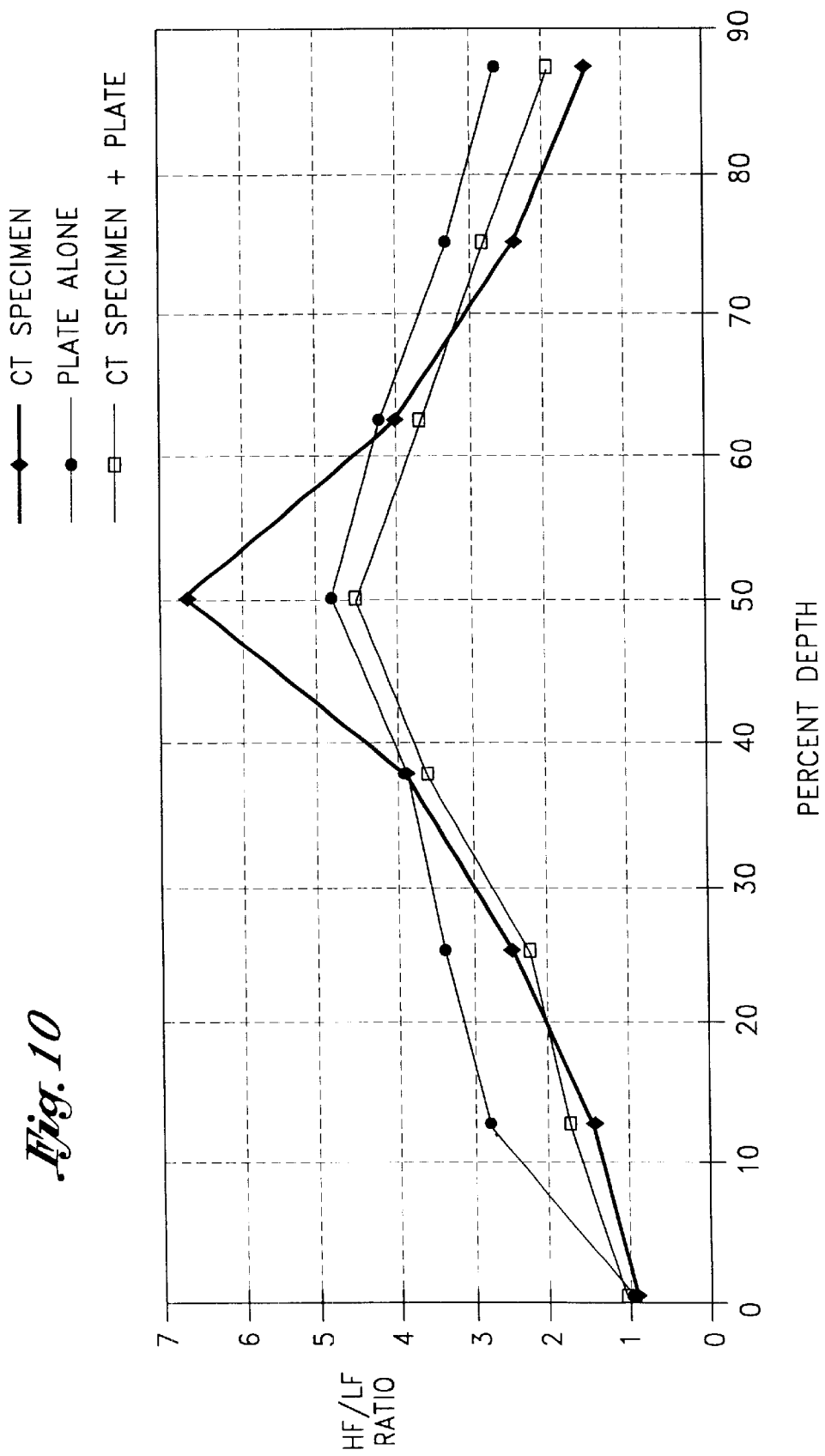
FIG. 10 is a calibration curve obtained with the apparatus of FIG. 8 to correlate frequency peak amplitude ratio with crack depth and to separate in-plane from out-of-plane signals.

A calibration curve based on the ratio of the peak amplitude of the high-frequency signal to the peak amplitude of the low-frequency signal is shown in FIG. 10. One can observe from the data in FIG. 10 that out-of-plane (OOP) sources for all three situations represented by FIG. 10 have ratios of less than one. A filter can therefore be constructed for data of this type by setting up the instrumentation and software to only accept as valid signals those signals having a high frequency to low frequency peak amplitude ratio greater than 1. Since extraneous noise sources are primarily OOP sources, they can be eliminated from the data set early by simple analog front end filtering as used in these experiments coupled with a simple software calculation and algorithm.

The methodology just described can also be used for field calibration of a field structure. The use of a calibration specimen is particularly advantageous in the field because the structure generally does not have an accessible edge for breaking pencil leads to simulate crack growth. The portability and adaptability of the instrumentation and apparatus of FIGS. 7 and 8 lend themselves to field testing.

It is very difficult to always put the same signal into the plate 314 with a pencil lead break. One must be very careful to hold the pencil parallel to the plane of the plate 314 when breaking the leads. Any force perpendicular to the plane of the plate 314 will tend to induce flexure waves in the plate 314. Because a ratio of two components of the same signal is computed, the ratio is not highly dependent on the absolute amplitude of the signal.

Breaking pencil lead on the surface of structures or specimens is generally not a good simulation of AE signals one might expect from crack growth in metals or fiber breakage in composites. It is very dependent on the location where the lead is broken and the pencil orientation in respect to the plane of the structure or specimen. The method and apparatus of simulating acoustic emission signals produced by crack growth with a structure are described in my patent, U.S. Pat. No. 5,014,556, which may be used in place of the pencil-break technique for improved performance, and is incorporated herein by reference.

2. Measurement

Once calibrated, the CT specimen or calibration block 310 is removed and a trigger transducer, such as transducer 318, is put in its place (not shown). Continuous monitoring of the crack proceeds and ratios are calculated for all received signals, as well as time of flight between the trigger transducer 318 and data transducer 322. The time of flight is used to construct a time-related filter. The ratio of each signal is calculated and signals that come from OOP sources are rejected. If a signal passes the ratio test, the time of flight between trigger transducer 318 and data transducer 322 is observed. If the time does not fall within a predetermined window, the data is rejected as coming from other cracks or extraneous sources. This forms a time-related filter or spatial filter for the signal. If the signal passes the time test, its ratio is compared to the calibration curve to estimate the depth of the crack responsible for the signal. As the crack continues to grow, it is observed whether or not the ratio is increasing or decreasing. If increasing, the crack is less than half way through the plate; if decreasing, the crack has passed the mid-plane of the plate 314 (FIG. 8). The trigger transducer 318 will allow the change in phase of the low frequency signal to be observed. This information can also be used to determine crack depth information.

E. Conclusions

This invention presents a new technique for using acoustic emission data to eliminate extraneous noise sources from a data base, and measure the depth of a growing crack in structures. This method can have tremendous impact on use of the technology for monitoring of structures in the field. Although the only information that can be measured is crack depth, it is the most important parameter affecting structural integrity for surface cracks. Some assumptions concerning the crack shape and physical measurement of the crack length at the surface allows one to determine the profile of the crack tip for a crack that has not penetrated through the thickness.

The simulated response of the data transducer 322 of FIG. 8 to crack growth may be validated by physically loading the specimen 310 after hydrogen charging to create crack growth, and correlating the AE data with actual crack growth.

It will be understood that the above-described arrangements of apparatus and the methods therefrom are merely illustrative of applications of the principles of this invention and many other embodiments and modifications may be made without departing from the spirit and scope of the invention as defined in the claims.

What is claimed is:

1. A system for substantially eliminating extraneous noise sources from the data produced during acoustic emission testing of a structure comprising:

a transducer coupled with said structure and configured to sense acoustic emission signal in said structure, said transducer being substantially equally sensitive to in-plane and out-of-plane acoustic emission signals;

a splitter which receives said signal from said transducer and divides said signal into a high-frequency signal and a low-frequency signal; and a circuit coupled to said splitter, said circuit generating a high-frequency peak amplitude and a low-frequency peak amplitude from said high-frequency and low-frequency signals; and a computer coupled to said circuit, said computer (i) computing the ratio of said high-frequency peak amplitude and said low-frequency peak amplitude; and (ii) accepting ratios indicative of crack growth and rejecting ratios indicative of extraneous noise.

2. A system for nondestructive testing of crack growth in a structure by detecting acoustic emission in the presence of extraneous noise signals comprising:

a transducer coupled to said structure producing an electrical signal including a high frequency component whose magnitude is substantially determined by the size of a crack or flaw in said structure and a low frequency component whose magnitude is substantially determined by extraneous noise;

a splitter coupled to said transducer;

a circuit coupled to said splitter, said circuit generating a peak amplitude corresponding to said high frequency component of the signal and a peak amplitude corresponding to said low frequency component of the signal; and a computer coupled to said circuit, said computer (i) computing the ratio of said high-frequency peak amplitude and said low frequency peak amplitude signals, (ii) comparing said ratio with a ratio value R that corresponds to extraneous noise signals, and (iii) providing outputs for ratio values greater than R indicative of crack growth.

3. A system for substantially eliminating extraneous noise sources from the data produced during acoustic emission testing of a structure comprising:

a transducer coupled to said structure producing an electrical signal including a high frequency component whose magnitude is substantially determined by the size of a crack or flaw in said structure and a low frequency component whose magnitude is substantially determined by extraneous noise; and computer means coupled to said transducer for (i) computing the ratio of said high-frequency peak amplitude and said low frequency peak amplitude components of the signal, (ii) comparing said ratio with a ratio value R that corresponds to extraneous noise signals, and (iii) providing outputs for ratio values greater than R indicative of crack growth.

4. A system for eliminating extraneous noise sources from the data produced during acoustic emissions testing comprising:

an acoustic emission sensor;

a high frequency and low frequency splitter coupled to said sensor; and a computer coupled to said high frequency and low frequency splitter for (i) computing the ratio of said high frequency component to low frequency component, and (ii) accepting ratios indicative of crack growth, and not accepting ratios correspond to extraneous noise.

5. A system for substantially eliminating extraneous noise sources from the data produced during acoustic emission testing of a structure comprising:

a transducer coupled with said structure and configured to sense acoustic emission signal in said structure, said transducer being substantially equally sensitive to in-plane and out-of-plane acoustic emission signals;

a splitter which receives said signal from said transducer and divides said signal into a high-frequency signal and a low-frequency signal; and a circuit coupled to said splitter, said circuit generating a high-frequency peak amplitude and a low-frequency peak amplitude from said high-frequency and low-frequency signals; and a computer coupled to said circuit, said computer computing the ratio of said high-frequency peak amplitude and said low-frequency peak amplitude.

* * * * *